US006878744B2

(12) United States Patent
Hegenauer

(10) Patent No.: US 6,878,744 B2
(45) Date of Patent: Apr. 12, 2005

(54) VITAMIN C COMPOSITIONS

(75) Inventor: John C. Hegenauer, Danville, CA (US)

(73) Assignee: Oxycal Laboratories, Inc., Prescott, AZ (US)

(*) Notice: Subject to any disclaimer, the term of this patent is extended or adjusted under 35 U.S.C. 154(b) by 0 days.

(21) Appl. No.: 10/362,867

(22) PCT Filed: Jun. 26, 2001

(86) PCT No.: PCT/US01/20431

§ 371 (c)(1),
(2), (4) Date: Jun. 27, 2003

(87) PCT Pub. No.: WO03/002113

PCT Pub. Date: Jan. 9, 2003

(65) Prior Publication Data

US 2004/0024053 A1 Feb. 5, 2004

Related U.S. Application Data

(63) Continuation-in-part of application No. PCT/US99/02735, filed on Feb. 5, 1999, now Pat. No. 6,197,813.

(51) Int. Cl.$^7$ .......................... A61K 31/35; A61K 31/34
(52) U.S. Cl. ...................... 514/460; 514/473; 514/474
(58) Field of Search ............................... 514/460, 473, 514/474

(56) References Cited

U.S. PATENT DOCUMENTS 6,197,813 B1 * 3/2001 Hegenauer ................. 514/474
6,468,980 B1 * 10/2002 Jariwalla ..................... 514/34

FOREIGN PATENT DOCUMENTS

WO          WO 01/15692       *   3/2001

* cited by examiner

*Primary Examiner*—Raymond J. Henley, III
(74) *Attorney, Agent, or Firm*—Drummond & Duckworth

(57) ABSTRACT

Vitamin C compositions comprise a Vitamin C compound, preferably a mineral ascorbate, and at least one compound of the group of 4-hydroxy-5-methyl-3(2H)-furanone and 3-hydroxy kojic acid.

4 Claims, No Drawings

VITAMIN C COMPOSITIONS

This application is a 371 of PCT/US01/29431, filed Jun. 26, 2001, which was a continuation-in-part of commonly owned International Application PCT/US99/02735, filed Feb. 5, 1999, now U.S. Pat. No. 6,197,813.

This invention relates to Vitamin C compositions.

More particularly, this invention relates to Vitamin C compositions suitable for preparing finished products such as cosmetic and dermatologic preparations, food products, e.g., processed foods, beverages, and nutritional supplements, and for preparing medicinal, dental, opthalmic and surgical compositions for both enteral and parenteral introduction.

Vitamin C has many known biological functions, e.g., acting as a wound healing accelerant, to prevent or treat periodontal disease, as an enzymatic co-factor, as a "sparing" agent against vitamin E depletion, as a collagen-synthesis stimulator, etc. Vitamin C is known to counteract oxygen-containing free radicals, including both the superoxide and hydroxyl radicals. These oxidative free radicals are generated in-vivo under a variety of normal and pathological conditions, and vitamin C is known for its ability to ameliorate conditions caused by oxygen free radicals, e.g., sunburn, cataracts, premature aging and a variety of other degenerative conditions.

The compositions of the invention comprise Vitamin C and a secondary component which is at least one compound selected from the group consisting of 4-hydroxy-5-methyl-3(2H)-furanone, 3-hydroxy-kojic acid, threose, erythreose, and 5-hydroxymaltol. According to the presently preferred embodiment of the invention, the Vitamin C component is a mineral ascorbate, i.e., a pharmacologically acceptable salt of ascorbic acid, including salts and complexes of ascorbate anions with pharmacologically acceptable cations of the alkali elements (sodium, potassium, etc.), alkaline-earth elements (calcium, magnesium, etc.), or transition elements (copper, iron, zinc, chromium, etc.).

In addition to the normal utility of the Vitamin C component, these compositions will induce improved dose-dependent, selective apoptosis of diverse human tumor cell-types, even though the concentration of the secondary component in these compositions is very low, i.e., from about 0.01 to about 1.0% by weight of the total composition.

The mineral ascorbates used in practicing the preferred embodiment of the invention are conveniently available as high-purity commercial products. If a single mineral ascorbate is used, it is presently preferred to use calcium ascorbate, although it is contemplated that two or even more mineral ascorbates may be employed, depending upon the end-use product involved.

Although calcium ascorbate is presently preferred, depending on the end-use of the finished products, other pharmacologically acceptable mineral ascorbates, illustratively, magnesium, sodium, potassium and/or zinc ascorbates and mixtures thereof are effectively employed.

The procedures for preparing the compositions of the invention are not critical and various modifications of the procedures described below will readily occur to persons skilled in the art having regard for these disclosures. In general the components are merely physically admixed and then tableted with tableting excipients, encapsulated or compression molded to provide convenient dosage forms. Alternatively, the compositions can be prepared as a stable liquid according to the processes disclosed in my issued U.S. Pat. No. 6,197,813.

EXAMPLES

The following examples are presented to aid in understanding the invention and to illustrate the presently preferred practice thereof. As illustrations, they are not intended to limit the scope of the invention, which is defined only by the appended claims.

Example 1

The following components are mixed to provide a composition with the components in the indicated percent by weight.

|  | Component | Wt. % |
| --- | --- | --- |
| PRODUCT A | calcium ascorbate | 95.00 |
|  | 4-hydroxy-5-methyl-3(2H)-furanone | 1.00 |
|  | Other (ascorbic acid, dehydroascorbic acid, etc.) | 4.00 |
| PRODUCT B | sodium ascorbate | 96.5 |
|  | 3-hydroxy-kojic acid | 0.2 |
|  | Other | 3.3 |

Example 2

This example illustrates the preparation of a food product, using the compositions of the invention, e.g., the compositions of Example 1.

500 ml of dry granulated sugar is added to 125 ml of water and 125 ml of corn syrup and the mixture is stirred and brought to boil at 150° C. Heating is discontinued and cherry flavoring is added to taste and desired color. Product A of Example 1 is added in the quantity required to obtain the desired Vitamin C content, e.g., 30 mg Vitamin C/g of "candy" food product. The composition and the sugar-syrup base are thoroughly mixed for sufficient time to fully disperse the concentrate product. Portions of the resulting hot mixture are transferred to the cavities a candy mold and cooled to form a Vitamin C enriched hard candy product.

Having described my invention in such terms as to enable those skilled in the art to understand and practice it and, having identified the presently preferred embodiments thereof, I claim:

1. A composition, comprising:
   (a) a vitamin C compound; and
   (b) at least one secondary compound selected from the group consisting of 4-hydroxy-5-methyl-3(2H)-furanone and 3-hydroxy-kojic acid.

2. The composition of claim 1 wherein said vitamin C compound is a mineral ascorbate.

3. The composition of claim 2 wherein said secondary compound is 4-hydroxy-5-methyl-3(2H)-furanone.

4. The composition of claim 2 wherein said secondary compound is 3-hydroxy-kojic acid.

* * * * *